(12) United States Patent
Lucas

(10) Patent No.: US 10,799,322 B2
(45) Date of Patent: Oct. 13, 2020

(54) ORAL ANTERIOR GUIDANCE PACKAGES, SYSTEMS, AND COMPONENTS

(71) Applicant: Kelly Lucas, Wasilla, AK (US)

(72) Inventor: Kelly Lucas, Wasilla, AK (US)

(73) Assignee: Kelly Lucas, Wasilla, AK (US)

( * ) Notice: Subject to any disclaimer, the term of this patent is extended or adjusted under 35 U.S.C. 154(b) by 88 days.

(21) Appl. No.: 15/793,135

(22) Filed: Oct. 25, 2017

(65) Prior Publication Data
US 2018/0042699 A1  Feb. 15, 2018

Related U.S. Application Data

(63) Continuation of application No. 13/774,033, filed on Feb. 22, 2013, now abandoned.

(51) Int. Cl.
*A61F 5/56* (2006.01)
*A61C 7/08* (2006.01)

(52) U.S. Cl.
CPC ............... *A61C 7/08* (2013.01); *A61F 5/566* (2013.01); *A61F 2005/563* (2013.01)

(58) Field of Classification Search
CPC ...... A61F 5/56; A61F 5/566; A61F 2005/563; A61C 7/08; A61C 7/36; A61C 2071/088; A61C 9/0006; A61B 71/085
USPC ............. 433/41–45; D24/156, 176, 180, 182
See application file for complete search history.

(56) References Cited

U.S. PATENT DOCUMENTS

| | | | |
|---|---|---|---|
| 1,734,398 A | 11/1929 | Phillips | |
| 2,027,373 A * | 1/1936 | Eden | A61C 19/05 |
| | | | 433/69 |
| 2,183,512 A * | 12/1939 | Brenner | A61C 19/05 |
| | | | 433/69 |
| 2,389,063 A | 11/1945 | Lang | |
| 2,481,203 A | 9/1949 | Davies et al. | |
| 2,529,429 A | 11/1950 | Spiro | |

(Continued)

FOREIGN PATENT DOCUMENTS

EP           0312368         4/1989

OTHER PUBLICATIONS http://www.nti-tss.com.

(Continued)

*Primary Examiner* — Anna K Kinsaul
*Assistant Examiner* — Camtu T Nguyen
(74) *Attorney, Agent, or Firm* — Troutman Pepper Hamilton Sanders LLP; Dustin B. Weeks; Brennan M. Carmody

(57) ABSTRACT

An oral anterior guidance system including: a mandibular retention piece; a mandibular guidance component coupled to the mandibular retention piece, the mandibular guidance including a convex outer surface proximate a first end; a maxillary retention piece; and a maxillary guidance component coupled to the maxillary retention piece, the maxillary guidance component including a concave inner surface, wherein the concave inner surface and the convex outer surface are configured to interact to guide movement of a patient's mandibular dental arch when the mandibular retention piece and the maxillary retention piece contact as the patient's mandibular dental arch closes, and wherein the mandibular guidance component is positioned anteriorly to an anterior of the anterior wall of the mandibular retention piece.

14 Claims, 6 Drawing Sheets

(56) References Cited

U.S. PATENT DOCUMENTS

| | | | |
|---|---|---|---|
| 3,069,774 | A | 12/1962 | Levy et al. |
| 3,134,152 | A | 5/1964 | Frush |
| 4,304,551 | A | 12/1981 | Kawasaki |
| 4,773,854 | A | 9/1988 | Weber |
| 4,901,737 | A | 2/1990 | Toone |
| 5,044,950 | A | 9/1991 | Hobish et al. |
| 5,059,120 | A | 10/1991 | Lee |
| 5,085,584 | A | 2/1992 | Boyd |
| 5,186,624 | A | 2/1993 | Gottsleben |
| 5,203,701 | A | 4/1993 | Burtch |
| 5,365,945 | A | 11/1994 | Halstrom |
| 5,427,117 | A | 6/1995 | Thornton |
| 5,722,828 | A | 3/1998 | Halstrom |
| 5,795,150 | A | 8/1998 | Boyd |
| 5,868,138 | A | 2/1999 | Halstrom |
| 6,041,784 | A | 3/2000 | Halstrom |
| 6,106,285 | A | 8/2000 | Kwak |
| 6,161,542 | A | 12/2000 | Halstrom |
| 6,666,212 | B2 | 12/2003 | Boyd, Sr. |
| 6,886,566 | B2 | 5/2005 | Eubank |
| 7,556,044 | B2 | 7/2009 | Ball |
| 7,654,267 | B2 | 2/2010 | Boyd |
| 8,156,940 | B2 | 4/2012 | Lee |
| 9,192,454 | B2 | 11/2015 | Klein et al. |
| 2002/0000230 | A1 | 1/2002 | Gaskell |
| 2005/0288624 | A1 | 12/2005 | Boyd |
| 2007/0099144 | A1 | 3/2007 | Keski-Nisula et al. |
| 2007/0079833 | A1 | 4/2007 | Lamberg |
| 2007/0178420 | A1 | 8/2007 | Keski-Nisula et al. |
| 2008/0000483 | A1 | 1/2008 | Halstrom |
| 2008/0099029 | A1 | 5/2008 | Lamberg |
| 2010/0147315 | A1 | 6/2010 | Chodorow |
| 2010/0279246 | A1 | 11/2010 | Keski-Nisula et al. |
| 2011/0030704 | A1 | 2/2011 | Hanna |
| 2011/0114100 | A1 | 5/2011 | Alvarez |
| 2011/0139162 | A1 | 6/2011 | Chodorow |
| 2011/0308532 | A1 | 12/2011 | Nelissen |
| 2012/0266896 | A1 | 10/2012 | Chodorow |
| 2012/0266897 | A1 | 10/2012 | Chodorow |
| 2012/0272972 | A1 | 11/2012 | Chodorow |
| 2013/0098375 | A1 | 4/2013 | Urbansk |
| 2013/0146067 | A1 | 6/2013 | Tschackert |

OTHER PUBLICATIONS http://www.greatlakesortho.com/content/files/resources/SplintAp-plianceSelectionGuide_S222.pdf.

Frank, et al., "Great Lakes Digital Splint," http://www.greatlakesortho.com/resource-center/digital-splints-users-group.

Maestre-Ferrin, L., et al., "Virtual articulator for the analysis of dental occlusion: An update," Med Oral Patol Oral Cir Bucal. vol. 17(1): e160-a163, Jan. 2012.

Solaberrieta, E., et al., "Design of a Virtual Articulator for the Simulation and Analysis of Mandibular Moments in Dental CAD/CAM," Proceedings of the 19th CIRP Design Conference-Competitive Design, pp. 323, Mar. 30-31, 2009.

* cited by examiner

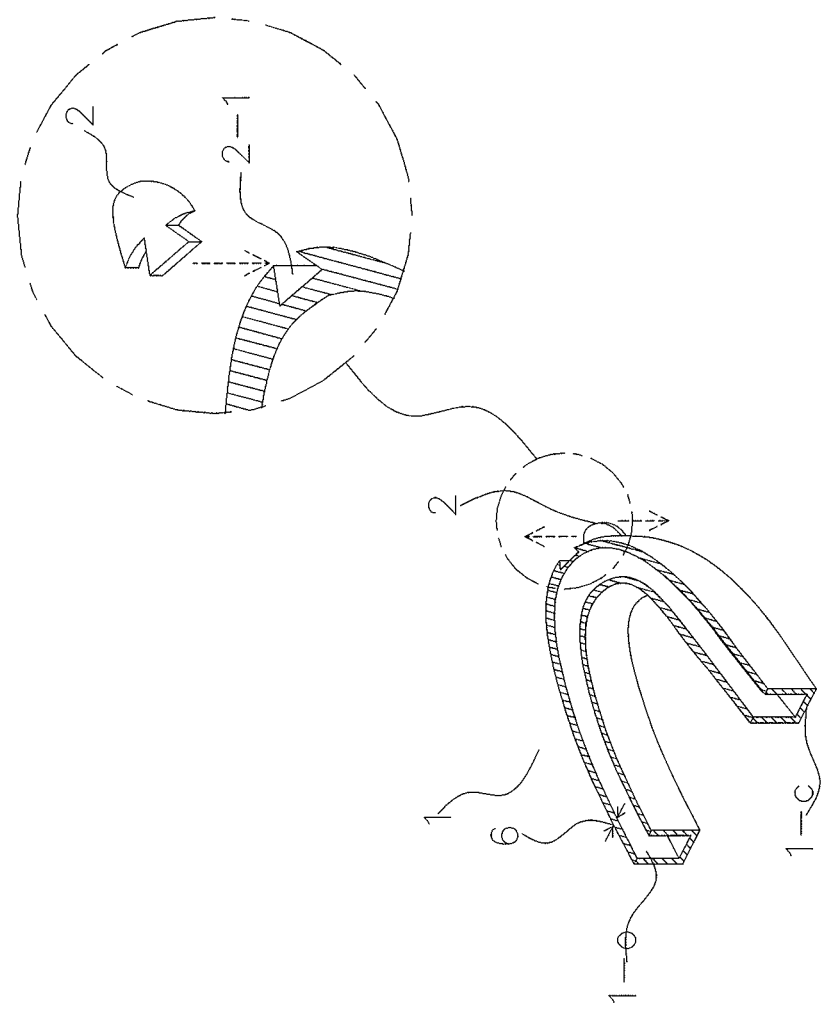
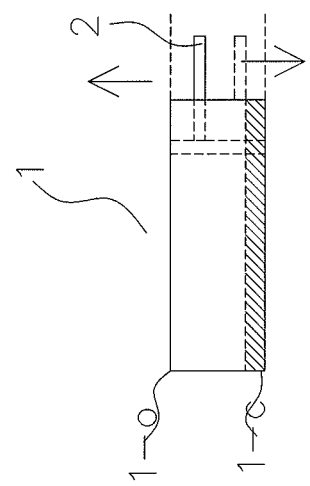
FIG. 1-a
FIG. 1-b

ORAL ANTERIOR GUIDANCE PACKAGES, SYSTEMS, AND COMPONENTS

CROSS-REFERENCE TO RELATED APPLICATIONS

This application is a continuation application of U.S. patent application Ser. No. 13/774,033 filed Feb. 22, 2013, the content of which is incorporated by reference herein in its entirety.

FIELD

Current application relates to a splint (night guard), especially relates to a splint for a bruxism patient with or without a severe malocclusion and gives the ability and option to the dentist to move the anterior guidance of a splint (night guard) anterior to existing teeth.

BACKGROUND

Many kinds of 'night guards' have been developed to ameliorate the negative impacts of bruxism. Simple coverage of teeth does help reduce damage to teeth by providing a barrier. However, without centric occlusion/centric relation (CO/CR) discrepancy correction and without anterior guidance, this type of night guard could actually cause increased severity of bruxism.

Appropriate anterior guidance in centric, long centric, straight protrusive and lateral excursions protects back teeth and reduces the muscle forces of bruxism because of the mechanically advantageous position of being anterior to the muscle power used to close the mandible. Traditionally, dentists have been able to improve CO/CR discrepancies and anterior guidance by creating a custom made and custom adjusted night guard, which typically is attached to the maxillary teeth. It is sometimes created on mandibular teeth. This appliance is custom built for a patient by a dentist considering their particular malocclusion and other factors allowing the mandible to be in centric relation with appropriate anterior guidance, and the elimination of posterior interferences, giving the patient significant relief from the damage and pain of bruxism. The applicant has provided an easy way of providing an appropriate night guard with the AGP (Anterior Guidance Package) in the previous U.S. patent application Ser. No. 13/573,283. Due to the unique properties of the AGP and the special retention piece of current application, a dentist has the ability for the first time to provide for a patient an appropriate splint (night guard) that provides anterior guidance ANTERIOR to the teeth. Anterior guidance can be provided independent of the limitations of where the teeth are and at a very minimal vertical dimension. Also in the case of a severe Class II or Class III malocclusion anterior guidance can be placed ANTERIOR to the physical limitations of the teeth of the deficient arch also with minimal increase in vertical dimension. It is the purpose of the current application to facilitate the use of the AGP for the direct fabrication of an AGP splint (night guard) that provides anterior guidance ANTERIOR to any limitations of teeth accomplishing that easier, less expensively, with minimal vertical dimension increase and a GREATER mechanical advantage over the muscles of mastication as compared to any previous night guard system.

DESCRIPTION OF RELATED ARTS

U.S. Patent Application Publications 2010/0279246, 2007/0178420, 2007/0099144 by Keski-Nisula; Katri; et al. disclose an odontological device and device series to guide an individual's occlusion and a method to be used in selecting an occlusion guidance appliance device to be used in orthodontic treatment. This kind of device contains a U-shaped arch with a lower surface on the side of the lower jaw and a higher surface on the side of the upper jaw, and in both of which there are concaves in which to place the individual's teeth, and where the bottoms of the concaves form of the isthmus separating the concaves from one another U.S. Patent Application Publication 20080000483, U.S. Pat. Nos. 6,161,542, 6,041,784, and 5,365,945 to Halstrom disclosed an intra-oral dental appliance for treatment of sleep disorders including snoring, sleep apnea and nocturnal bruxism. The appliance includes an upper member conforming to the patient's maxillary dentition; a lower member conforming to the patient's mandibular dentition; and a connecting assembly for adjustable coupling of the upper and lower members together. The only benefit in regard to bruxism is that Halstrom's appliance does separate teeth therefore damage to teeth would be eliminated. However, his connecting assembly limits the movement of the jaw. This may cause many problems because the major goal of treatment for tooth damage, myofacial pain, migraines etc. secondary to bruxism, is to allow the jaw (mandible) freedom to relax to its most comfortable position. This position would be centric relation for 99% of people. Centric relation allows the jaw to be in its most anatomically correct stress bearing position and the place where the muscles are most calm. Dentists use centric relation or an even more refined point to create a night guard that allows the mandible to rest there and then guidance from that position to avoid posterior interferences and freedom so the jaw can move, the patient can yawn, open, sneeze, breathe, swallow etc. normally.

When a person, having a malocclusion, maximally intercuspates their teeth as in bruxism, the jaw is forced to adapt a position other than centric relation. Because of muscle engrams the jaw ends up living in this inappropriate position. Secondly, by locking the lower jaw forward in relation to the upper jaw over time, which will happen when a person wears Halstrom's appliance, the person may experience unintended and inappropriate orthodontic movement of the teeth that create or make worse a malocclusion. Third, by locking the lower jaw forward in relation to the upper jaw you have pulled the mandibular condyle down the articular imminence to a very inappropriate position (not in the fossa). It may prevent damage to teeth but if the person exerts muscle activity in that position, one is more likely to damage the TMJ. One major purpose of a night guard is to allow the persons jaw to assume the position of centric relation, not purposely pull the jaw into some other position.

Myofacial pain would be terrible for a person wearing this type appliance since the condyles and muscles of mastication are artificially pulled into very inappropriate positions. U.S. Patent Application Publication 2005/028862S., U.S. Pat. Nos. 7,654,267, 5,795,150, and 5,085,584 by Boyd, and U.S. Pat. No. 6,666,212 to Boyd. Sr., illustrate an intraoral discluder for preventing chronic tension headaches, common migraine headaches, and temporo-mandibular disorders that are caused or perpetuated by chronic activity of the temporalis muscle. The discluder includes a trough, contoured to encompass at least one maxillary or mandibular incisor, from which extends a protruding platform, for engagement by the opposing incisors. The trough can be retained on the teeth by any adaptable material than can flow around the teeth and then maintain its shape. Once in place in the wearer's mouth, one or two opposing incisors will come into contact with the platform prior to the upper and lower posterior and/or canine teeth coming into contact, regardless of the position of the mandible, thereby reducing the intensity of the activity of the temporalis muscle. In addition, a special post on the discluder's platform is engageable directly with one or more opposing incisors, to act as a stop and thereby inhibit excessive retrusive movement of the mandible and urge the mandible toward a more protrusive position. This can reduce the intensity of undesired clenching, and it can enhance the size of the wearer's pharyngeal airspace, thereby reducing the incidence and severity of snoring. However, Boyd's invention did not consider patients who have severe malocclusions, loss of teeth, and periodontally weakened teeth, etc. If a patient with such abnormalities wears Boyd's intraoral discluder and brux while sleeping, it will make the patient's abnormalities worse. Also as compared to the AGP combined with the special tray of current application, the vertical dimension increase of Boyds device to overcome posterior interferences quickly becomes excessive to the point the patient may not be able to wear it. Also, in Boyds device anterior disclusion is tied to the position of teeth in contrast to the AGP and the current application, which allows not just disclusion, but true guidance, independent of the position of the patient's teeth.

U.S. Pat. No. 4,773,854 to Weber disclosed herein is a device for the representation of condylar movements of a patient and their correct simulation which includes models of sets of teeth to determine the required corrections to the biting surfaces in order to obtain ideal occlusion. The device includes an articulator with the lower part thereof able to be brought into a predetermined three-dimensional relation with respect to an upper part of the articulator and having two blocks having guide elements on the lower part of the articulator to support condyle balls of the upper part of the articulator. The device further includes a lower jaw recording bow and an upper jaw recording bow which can be brought into an active and predetermined relation with respect to the articulator and which disposes of at least three recording plates with corresponding recording pins as well as positioning spoons for the combination of a lower jaw dentition model. With this device, opening movements of articulation may be recorded three-dimensionally so that three clear crossing points are created for the occlusion.

U.S. Pat. No. 4,901,737 to Toone discloses an intra-oral appliance for reducing snoring, which repositions the mandible in an inferior (open) and anterior (protrusive) position as compared to the normally closed position of the jaw. Once the dentist or physician determines the operative "snore reduction position" for a particular patient, an appropriate mold is taken of the maxillary dentition and of the mandibular dentition for formation of the appliance template. The Toone appliance includes a pair of V-shaped spacer members formed from dental acrylic, which extend between the maxillary and mandibular dentition to form a unitary mouthpiece. In an alternative embodiment of the Toone invention, the spacer members are formed in two pieces and a threaded rod is provided to enable adjustment of the degree of mandibular protrusion or retrusion after the mouthpiece is formed.

European patent application No. 0,312,368 published also discloses an intra-oral device for preventing snoring. This device consists of a U-shaped mouthpiece, which conforms to the upper dental arch of the user and includes a sloped, lower ramp for engaging the mandibular dentition. Normal mouth motions, such as the clenching of the jaw, will cause some of the mandibular dentition to engage the underside of the ramp, thereby camming the lower jaw forward to increase the spacing between the base of the tongue and the posterior wall of the pharynx. U.S. Pat. No. 5,722,828 to Halstrom discloses an apparatus and method for producing a gothic arch tracing representative of the natural range of motion of a patient's mandible. The apparatus consists of a kit including a mandibular bite rim having a tracing plate; a maxillary bite rim having a tracing arm; and a stylus reversibly connectable to the tracing arm for extending between the tracing arm and the tracing plate externally of the patient's mouth. The stylus has a marker on one end thereof for drawing a gothic arch tracing on a removable paper substrate, such as a post-it note, attachable to the tracing plate. The tracing is used in the fabrication of a dental bite registration mold for the patient. The mold may in turn be used to mount casts of the patient's dentition in a specific relationship as required for prosthetic or therapeutic purposes. Frank et al, disclosed a full contact splint with anterior guidance (see Great Lakes Orthodontics, Splint Appliance Selection Guide, S222,). The full contact splint with anterior guidance is to form an anterior guidance under the lower surface of the maxillary retentive piece. However, developing anterior guidance directly to the lower surface of the maxillary retentive piece is a very time-consuming trial and error job, and is expensive for both the dentist and patient.

From the above prior arts, it is found that none of the prior art provides an economical, easy to apply and medically safe anterior guidance splint (night guard) for patients as provided by the special retention piece of current application combined with an AGP, to include patients with severe Class II or Class III malocclusions. Also, no prior art provides for anterior guidance that is not tied to and dependent upon the position of anterior teeth. In contrast to all prior arts, the AGP combined with the special retention piece of the current application can provide a splint (night guard) with optimal anterior guidance, which eliminates all posterior interferences, and can be located ANTERIOR to any limitations of teeth therefore increasing the mechanical advantage of that guidance over the muscles of mastication.

SUMMARY

Many kinds of 'night guards' have been developed to ameliorate the negative impacts of bruxism. Simple coverage of teeth does help reduce damage to teeth by providing a barrier. However, without centric occlusion/centric relation (CO/CR) discrepancy correction and without anterior guidance, this type of night guard could actually cause increased severity of bruxism. Appropriate anterior guidance in centric, long centric, straight protrusive and lateral excursions protects back teeth and reduces the muscle forces of bruxism because of the mechanically advantageous position of being anterior to the muscle power used to close and brux with the mandible. Traditionally, dentists have been able to improve CO/CR discrepancies and anterior guidance by creating a custom made and custom adjusted night guard, which typically is attached to the maxillary teeth. It can also be fabricated on mandibular teeth. This appliance is custom built for a patient by a dentist considering their particular malocclusion and other factors allowing the mandible to be in centric relation with appropriate anterior guidance giving the patient significant relief from the damage and pain of bruxism. The applicant has provided an easy way of providing an appropriate night guard with the AGP (Anterior Guidance Package) in the previous U.S. patent application Ser. No. 13/573,283. However, a special retention piece, AGP (Anterior Guidance Package) equipped night guard, is provided. Due to the unique properties of the AGP and the special retention piece of current application, a dentist has the ability for the first time to provide, for a patient, an appropriate splint (night guard) that provides anterior guidance ANTERIOR to the teeth. Anterior guidance can now be provided independent of the limitations of where the teeth are located and at a very minimal vertical dimension. Also in the case of a severe Class II or Class III malocclusion anterior guidance can be placed ANTERIOR to the physical limitations of the teeth of the deficient arch, also with minimal increase in vertical dimension. It is the purpose of the current application to facilitate the use of the AGP for the direct fabrication of an AGP splint (night guard) that provides anterior guidance ANTERIOR to any limitations of teeth, accomplishing that easier, less expensively, with minimal vertical dimension increase and a GREATER mechanical advantage over the muscles of mastication as compared to any previous night guard system. A special retention piece of the current application combined with the AGP (Anterior Guidance Package) is provided. The AGP splint (night guard) combined with special retention pieces is comprised of 1) one AGP (Anterior Guidance Package) and 2) two special retention pieces having an anteriorly protruded shelf to receive the maxillary guidance component of the AGP and the mandibular guidance component of the AGP. For a severe Class II malocclusion patient, the AGP night guard is comprised of; 1) one AGP (Anterior Guidance Package), 2) one special retention piece of the current application to receive the mandibular guidance component of the AGP and 3) one regular retention piece to apply the maxillary guidance component of the AGP. For a severe Class III malocclusion patient the AGP night guard is comprised of; 1) one Anterior Guidance Package, 2) one special retentive piece of the current application to receive the maxillary guidance component of the AGP and 3) one regular retention piece to apply the mandibular guidance component of the AGP.

BRIEF DESCRIPTION OF THE FIGURES

FIG. 1-a is a perspective view of the special retention piece of the current application.

FIG. 1-b is a side view of the special retention piece of the current application.

DETAILED DESCRIPTION

Anterior guidance provides physical guidance and limits to the front end of the mandible. Anterior guidance reduces the forces of the muscles of mastication by the unique attribute of being located anterior to the muscles used to brux. This is explained in more detail in the applicant's previous U.S. patent application Ser. No. 13/573,283. In a bruxism patient the further anterior the guidance, the more force reduction is experienced. The special retention piece (1) of the current application can be used as a maxillary retention piece and/or as a mandibular retention piece. Two special retention pieces (1) can be used simultaneously on both arches. The special retention piece (1) of the current application can be used as a maxillary retention piece or used as a mandibular retention piece combined with a regular retention piece based on the type and severity of a malocclusion.

FIG. 1a is a perspective view of the special retention piece (1) of the current invention for the maxilla or mandible. FIG. 1-b is the side view thereof. The special retention piece (1) for the maxilla or mandible has a shelf (2) to receive the appropriate component of AGP (Anterior Guidance Package). The shelf (2) is located on the most anterior aspect of the retention piece (1). Vertical position of the shelf (2) may vary from the open side (1-O) of the groove that molds to the teeth down to the closed side (1-C) of the groove of the retention piece (1). The shelf (2) is inserted to a groove (2-1), which is vertically developed on the anterior surface of the special retention piece (1)

Figure 2:
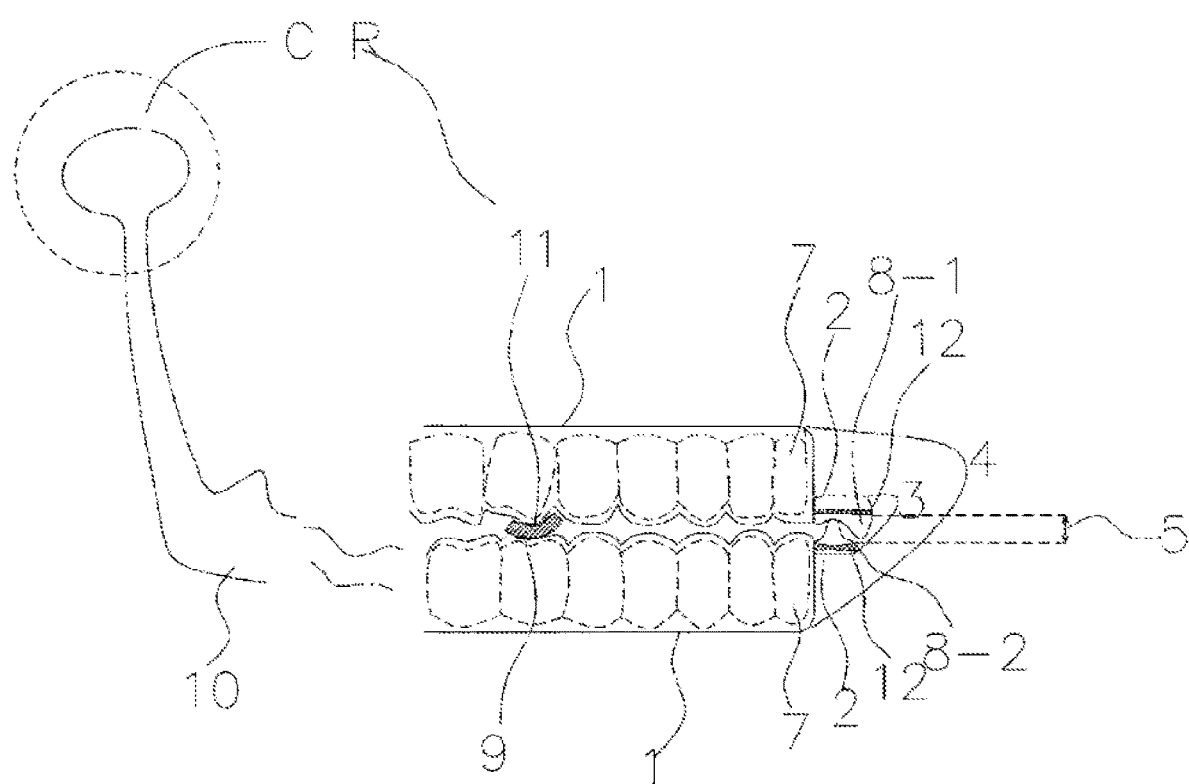
FIG. 2 is a schematic drawing that shows how to use the special retention pieces as retentive pieces and platforms for the AGP for both the maxillary and mandibular arches simultaneously to allow the placement of the AGP anterior to the front teeth to comprise a special splint.

The special retention piece (1) of the current application is moldable, retentive, stiff, and thin. FIG. 2 is a schematic drawing that shows how the special retention piece (1) can be used for both the maxillary and mandibular retentive pieces to enable the AGP (3) to be placed anterior to the anterior teeth to comprise a splint (4) that is a combination of the special retention pieces (1) and an AGP (3).

One major advantage of the AGP (3) is that anterior guidance is not dependent upon teeth. One way to exploit this unique characteristic of the AGP (3) and improve the performance of a night guard, as shown in FIG. 2, is to place the AGP (3), and therefore the anterior guidance further anterior than where the anterior teeth are located.

This strategy can increase the mechanical advantage of the AGP (3) over the muscles of mastication in contrast to any previous system.

Another advantage over any previous night guard system that the AGP (3) has, by placing the AGP (3) further anterior than the actual position of the anterior teeth (7) would dictate, is the ability to provide anterior guidance in a splint with extremely minimal vertical dimension (5) increase. Since the AGP (3) is located ANTERIOR to the anterior teeth (7), the material required to provide the anterior guidance correction is not in addition to that of the anterior teeth (7), but rather anterior to and independent of anterior teeth (7). This minimal vertical dimension (5) made possible by the AGP (3) combined with the special retentive pieces (1) increases patient's acceptance and comfort dramatically.

Figure 3:
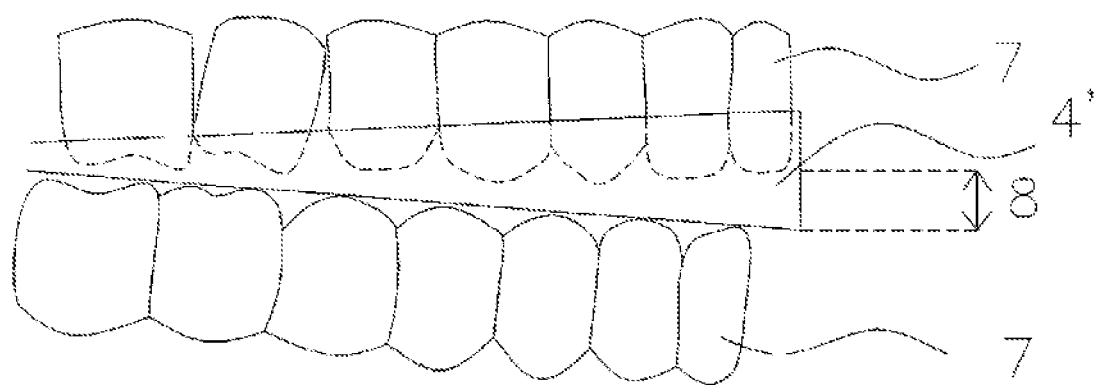
FIG. 3 is a schematic drawing of a traditional night guard showing anterior guidance correction, which adds bulk in the vertical dimension in addition to the anterior teeth, and shows the anterior teeth's relative position to this guidance correction in prior arts.

FIG. 3 is a schematic drawing of traditional splint (4') and the anterior teeth (7)'s relative location of prior arts. In all previous splint systems, the splint (4') was dependent upon where the anterior teeth (7) were located so the splint (4') was placed in between top and bottom front (anterior) teeth (7) or was put in an acrylic splint opposing natural dentition anterior teeth. Therefore, to eliminate posterior interferences the vertical dimension (8) of these splints were in addition to anterior teeth (7) and were often thick with excessive vertical dimension increase, even when the jaw was at rest in centric relation.

In summary, one of the major advantages of the special retention piece (1) of the current application combined with the AGP (3) over any previous system is the ability to place the AGP (the anterior guidance for the mandible) anterior to the physical limitations of the teeth. This characteristic only found in the AGP increases the mechanical advantage over the muscles used to brux, and also provides to the patient a night guard that has a significantly smaller vertical dimension footprint, like the vertical dimension in FIG. 2.

In contrast to all previous splint (night guard) systems, the AGP combined with the special retention pieces of current application, provides a splint (4), that when worn by the patient provides anterior guidance and posterior interference elimination with a minimum of vertical dimension (5) increase. Indeed, the vertical dimension (5) increase would represent only the thickness (6) of the retention piece (1) material, which could be as little as 1 mm, on the patient's teeth because all the functional apparatus of the AGP (3) is located anterior to the front teeth so appropriate anterior guidance is provided without increasing the vertical dimension, in contrast to modifying anterior guidance with acrylic in addition to vertical dimension of the anterior teeth (7). The vertical location of the shelf (2) can be adjusted, via proper methods including but not limited to gluing to the anterior surface of the special retention piece (1) or the shelf (2) is molded when molding the retention piece, to match to the height of the AGP (3) minimizing the amount of adhesive filler used, and to minimize the size of the guidance package in the finished AGP night guard for greater lip comfort.

To take advantage of this major benefit made possible by the AGP (3), an operator can place the AGP (3) in an anterior position to the teeth in one of several ways:

1. A CAD-CAM produced AGP splint (4) made from records of the patient. This patent will be provided in a separate filing by the applicant.
2. An indirect lab produced AGP splint (4) made from records of the patient. A lab would use these special retention pieces and an AGP, but the splint would be made indirectly.
3. Direct anterior placement of the AGP (3) with a kit using special retention pieces (1): For this the special retention pieces (1) are provided which can be used with a direct placement AGP splint Kit (8) in a dental clinic. The AGP splint kit (8) is comprised of a maxillary guidance component (8-1), a mandibular guidance component (8-2) and a holder (13) that temporarily holds the two components (8-1) and (8-2) together in their appropriate (centric relation) position to each other.

Figure 4:
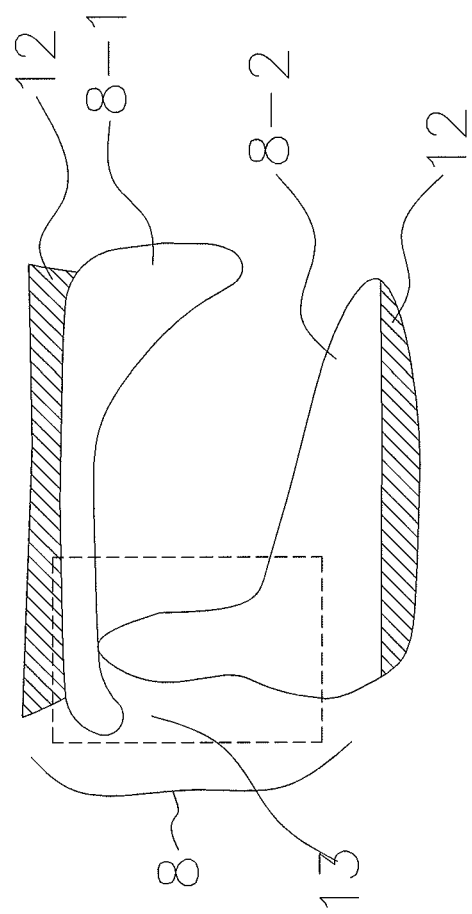
FIG. 4 is a side view of an AGP kit.

FIG. 4 is a side view of the AGP kit (8) used for the current application. It is explained in more detail in the current applicant's previous U.S. patent application Ser. No. 13/573,283.

The AGP (3) could be delivered from the manufacturer already attached to a retentive piece for one arch (maxillary or mandibular arch) and then indexed onto a retentive piece molded to the other arch, or the AGP (3) could be indexed by the dentist onto the shelf or shelfs of the special retention piece or pieces.

AGP Splint Set Up

To construct an AGP splint (4) with two special retention pieces (1) the operator, probably a dentist will gather as pictured in FIG. 2, an AGP Kit (8), two special retention pieces (1) and a 1 mm sticky but removable spacer (9).

With the above materials, the operator:
1. Molds the maxillary and mandibular special retention pieces (1) of current invention onto the maxillary and mandibular teeth respectively.
2. Hinges the mandible (10) up in centric relation (CR) and places the 1 mm sticky but removable spacer (9) on the first contact (11).
3. Places adhesive filler (12) on the superior and inferior surfaces of the AGP kit (8) and hinges the mandible (10) up in centric relation (CR) again, and indexes the AGP kit (8) between the shelves (2) of the maxillary and mandibular special retention pieces (1). Vertical dimension of the shelves (2) is adjusted by moving the shelves (2) vertically along the groove (2-1), wherein the shelf (2) is inserted.
4. Dries or cures the adhesive filler (12) rigidly securing the AGP (3) to both retention pieces (1) with the mandible (10) in centric relation (CR) and a minimal and appropriate vertical dimension.
5. Removes the entire assembly, removes the 1 mm sticky but removable spacer (9), removes the holder (13) from the AGP kit (8) and the AGP Night Guard is ready for use. What we have now provided is an ideal anterior guidance night guard, AGP splint (4), which eliminates all posterior interferences and does that with a vertical dimension only 1 mm greater than the worst posterior interference in centric relation plus the thickness of the retention piece (6). It also provides this anterior guidance in a superior mechanical position for advantage over the muscles of mastication.

Figure 5:
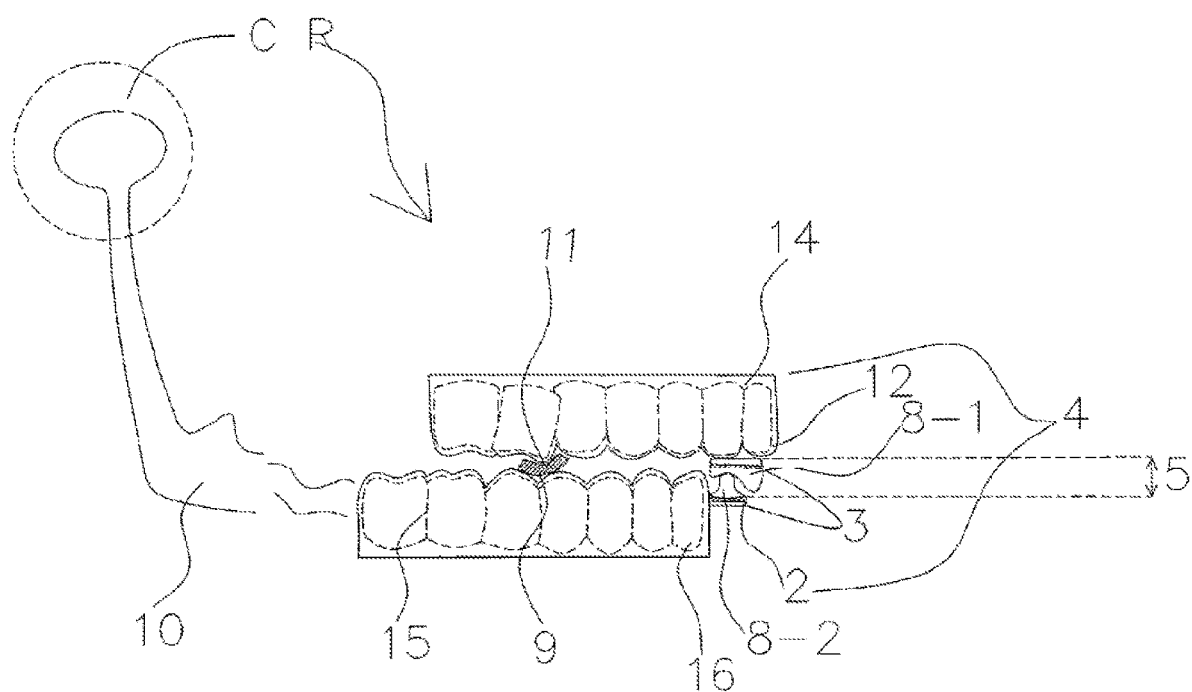
FIG. 5 is a schematic drawing that shows the use of one special retention piece of current application and one regular retention piece for a patient who presents with a significant Class II malocclusion.

FIG. 5 shows the use of one special retention piece (1) of current invention and one regular retention piece (14) for a patient who presents with a significant Class II malocclusion. The special retention piece (1) is used on the retrognathic mandibular arch (15) and allows placing the AGP (therefore anterior guidance) (3) anterior to the anatomical position of the mandibular front teeth (16). As shown in the FIG. 5, the vertical dimension (5) of the AGP splint (4) is minimized by combining the special retention piece (1) of the current application and a regular retention piece (14). Therefore, a patient suffering significant Class II malocclusion and bruxism will have a night guard with much greater mechanical advantage and more comfortable than any of the previous night guard systems due to minimal vertical dimension increase. Also, a dentist can provide a proper night guard for a patient who has these problems with much less effort. The procedure for setting up an AGP night guard for a severe Class II malocclusion case is the same as the above-described procedure of AGP splint set up 1 to 5.

Figure 6:
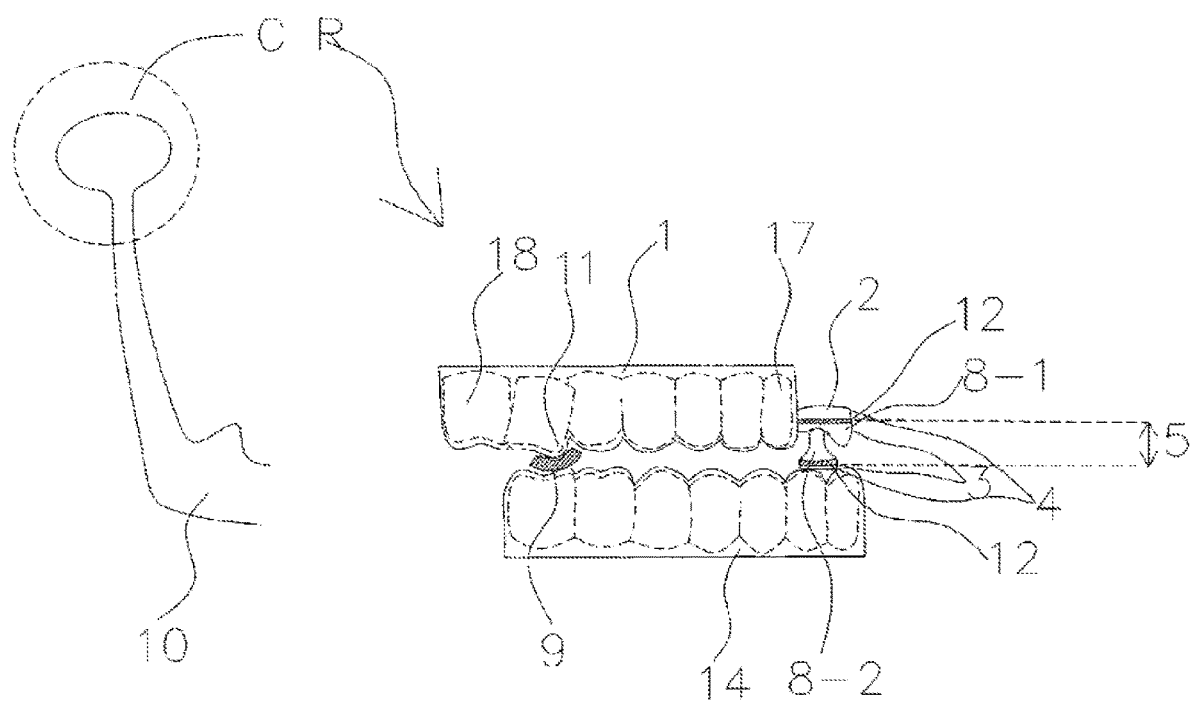
FIG. 6 is a schematic drawing that shows the use of one special retention piece of current invention and one regular retention piece for a patient who presents with a significant Class III malocclusion.

FIG. 6 shows the use of one special retention piece (1) of current invention and one regular retention piece (14) for a patient who presents with a significant Class III malocclusion. The special retention piece (1) is used on the maxillary arch (18) so the AGP can be placed anterior to the anatomical limitation of the maxillary front teeth (17). FIG. 6 shows the use of one special retention piece (1) of current invention and one regular retention piece (14) for a patient who presents with a significant Class III malocclusion. The special retention piece (1) is used on the maxillary arch (18) so the AGP can be placed anterior to the anatomical limitation of the maxillary front teeth (17).

As shown in the FIG. 6, the vertical dimension (5) of the AGP splint (4) is minimized by combining the special retention piece (1) of the current application and a regular retention piece (14). Therefore, a patient suffering significant Class III malocclusion and bruxism will have a night guard with much greater mechanical advantage, and is more comfortable than any of the previous night guard systems, because of minimal vertical dimension increase. Also, a dentist can provide a proper night guard for a patient who has these problems with much less effort. The procedure for setting up an AGP night guard (4) for severe Class III malocclusion case is the same as the above-described procedure of AGP splint set up 1 to 5.

In conclusion, in contrast to all previous systems, for the bruxism patient, ideal anterior guidance and the elimination of posterior interferences at a very minimal increase in vertical dimension can now be provided easily and simply regardless the malocclusion, missing teeth, or the condition of teeth using the AGP and the special retentive piece.

In contrast to all previous systems, the AGP combined with special retentive piece can provide guidance without regard to the current position of teeth, therefore the AGP can be placed anterior to the patient's teeth according to current application.

What is claimed is:

1. An oral anterior guidance system for treating a patient having a mandibular dental arch and a maxillary dental arch, the system comprising:
    a mandibular retention piece for placement about the mandibular dental arch;
    a mandibular guidance component coupled to the mandibular retention piece, the mandibular guidance component having opposing first and second ends, wherein the mandibular guidance component comprises a convex outer surface proximate the first end;
    a maxillary retention piece configured to oppose the mandibular retention piece, the maxillary retention piece for placement about the maxillary dental arch; and
    a maxillary guidance component coupled to the maxillary retention piece, the maxillary guidance component comprising a concave inner surface,
    wherein the concave inner surface of the maxillary guidance component and the convex outer surface of the mandibular guidance component are configured to interact to guide movement of the mandibular dental arch relative to the maxillary dental arch to centric relation when the mandibular retention piece and the maxillary retention piece contact as the mandibular dental arch closes,
    wherein the mandibular retention piece comprises:
        a channel formed between anterior and posterior walls, the channel being configured to accept teeth of the patient when the mandibular retention piece is placed about the mandibular dental arch,
        a vertical groove in an anterior surface of the anterior wall of the mandibular retentive piece, and
        a platform extending anteriorly from the anterior wall, the platform being insertable and vertically adjustable within the vertical groove, and
    wherein the mandibular guidance component is positioned anteriorly to anterior wall and coupled to the platform.

2. The oral anterior guidance system of claim 1, wherein the maxillary guidance component is positioned about a lower surface of the maxillary retention piece.

3. The oral anterior guidance system of claim 2, wherein a vertical position of the mandibular guidance component relative to the mandibular retention piece is adjustable.

4. The oral anterior guidance system of claim 1, wherein the maxillary retention piece comprises a channel formed between anterior and posterior walls, and
    the maxillary guidance component is positioned anteriorly and exteriorly to the anterior wall of the maxillary retention piece.

5. The oral anterior guidance system of claim 4, wherein a vertical position of the maxillary guidance component relative to the maxillary retention piece is adjustable.

6. The oral anterior guidance system of claim 4, wherein a vertical position of both of the maxillary guidance component relative to the maxillary retention piece and the mandibular guidance component relative to the mandibular retention piece are adjustable.

7. An oral anterior guidance system for treating a patient having a mandibular dental arch and a maxillary dental arch, comprising:
    a mandibular retention piece for placement about the mandibular dental arch;
    a mandibular guidance component formed by an upwardly-extending protrusion of the mandibular retention piece, the mandibular guidance component having opposing first and second ends, wherein the mandibular guidance component comprises a convex outer surface proximate the first end;
    a maxillary retention piece configured to oppose the mandibular retention piece, the maxillary retention piece for placement about the maxillary dental arch; and
    a maxillary guidance component formed by a downwardly-extending protrusion of the maxillary retention piece, the maxillary guidance component comprising a concave inner surface,
    wherein the concave inner surface of the maxillary guidance component and the convex outer surface of the mandibular guidance component are configured to interact to guide movement of the mandibular dental arch relative to the maxillary dental arch to centric relation guide movement of the mandibular dental arch relative to the maxillary dental arch to centric relation when the mandibular retention piece and the maxillary retention piece contact as the mandibular dental arch closes, and
    wherein the maxillary retention piece comprises:
        an anterior portion configured to be exterior to the maxillary dental arch when placed about the respective mandibular and maxillary dental arch,
        a vertical groove in an anterior surface of the anterior portion, and
        a platform extending anteriorly from the anterior portion, the platform being insertable and vertically adjustable within the vertical groove, and
    wherein the maxillary guidance component is positioned anteriorly to the anterior portion of the maxillary retention piece and coupled to the platform.

8. The oral anterior guidance system of claim 7, wherein the mandibular retention piece comprises an anterior portion configured to be exterior to the mandibular dental arch when the mandibular retention piece is placed about the mandibular dental arch,
    the upwardly-extending protrusion forming the mandibular guidance component is disposed anteriorly to the anterior portion of the mandibular retention piece.

9. The oral anterior guidance system of claim 8, wherein at least a portion of one of the downwardly-extending protrusion and the upwardly-extending protrusion is vertically adjustable with respect to its respective retention piece.

10. The oral anterior guidance system of claim 7, wherein the upwardly-extending protrusion forming the mandibular guidance component extends from an upper surface of the mandibular retention piece.

11. The oral anterior guidance system of claim 10, wherein at least a portion of one of the downwardly-extending protrusion and the upwardly-extending protrusion is vertically adjustable with respect to its position about its respective retention piece.

12. The oral anterior guidance system of claim 10, wherein at least a portion of both of the downwardly-extending protrusion and the upwardly-extending protrusion are vertically adjustable with respect to their positions about their respective retention pieces.

13. An oral anterior guidance system for treating a user having a mandibular dental arch and a maxillary dental arch, comprising:
- a mandibular retention piece for placement about the mandibular dental arch;
- a mandibular guidance component formed by an upwardly-extending protrusion of the mandibular retention piece, the mandibular guidance component having a first end and a second end, wherein the mandibular guidance component comprises a convex outer surface proximate the first end;
- a maxillary retention piece configured to oppose the mandibular retention piece, the maxillary retention piece for placement about the maxillary dental arch; and
- a maxillary guidance component formed by a downwardly-extending protrusion of the maxillary retention piece, the maxillary guidance component comprising a concave inner surface, wherein the concave inner surface of the maxillary guidance component and the convex outer surface of the mandibular guidance component are configured to interact to guide movement of the mandibular dental arch relative to the maxillary dental arch to a refined point, wherein the mandibular retention piece comprises:
- a vertical groove in an anterior surface of the mandibular retentive piece, and
- a platform extending anteriorly from the anterior surface, the platform being insertable and vertically adjustable within the vertical groove, and wherein the mandibular guidance component is positioned anteriorly to the anterior surface and connected to the platform.

14. The oral anterior guidance system of claim 13, wherein the maxillary guidance component is configured to extend anteriorly beyond the maxillary retention piece and past the maxillary dental arch when the maxillary retention piece is placed about the maxillary dental arch.

* * * * *